United States Patent
Kraus et al.

(10) Patent No.: US 8,109,908 B1
(45) Date of Patent: Feb. 7, 2012

(54) BIODEGRADABLE SHROUD FOR A DILATOR/SHEATH ASSEMBLY

(75) Inventors: Mark C. Kraus, Independence, MN (US); Qingshan Ye, Plymouth, MN (US)

(73) Assignee: Greatbatch Ltd., Clarence, NY (US)

( * ) Notice: Subject to any disclaimer, the term of this patent is extended or adjusted under 35 U.S.C. 154(b) by 398 days.

(21) Appl. No.: 12/357,732

(22) Filed: Jan. 22, 2009

Related U.S. Application Data

(60) Provisional application No. 61/022,651, filed on Jan. 22, 2008.

(51) Int. Cl.
*A61M 5/178* (2006.01)
(52) U.S. Cl. .................................. 604/164.03
(58) Field of Classification Search ............. 604/164.08, 604/164.09–164.12, 171–172, 103.05–103.06
See application file for complete search history.

(56) References Cited

U.S. PATENT DOCUMENTS

| | | | |
|---|---|---|---|
| 4,827,940 A * | 5/1989 | Mayer et al. ............ | 600/375 |
| 4,876,109 A | 10/1989 | Mayer et al. | |
| 5,531,783 A | 7/1996 | Giele et al. | |
| 5,994,444 A | 11/1999 | Trescony et al. | |
| 6,304,786 B1 | 10/2001 | Heil, Jr. et al. | |
| 6,409,674 B1 | 6/2002 | Brockway et al. | |
| 6,522,915 B1 | 2/2003 | Ceballos et al. | |
| 6,584,363 B2 | 6/2003 | Heil, Jr. et al. | |
| 6,631,290 B1 | 10/2003 | Guck et al. | |
| 6,939,328 B2 * | 9/2005 | Raulerson ............ | 604/175 |
| 7,089,046 B2 | 8/2006 | Heil, Jr. et al. | |
| 2001/0049502 A1 | 12/2001 | Chen | |
| 2003/0233115 A1 | 12/2003 | Eversull et al. | |
| 2005/0113900 A1 | 5/2005 | Shiroff et al. | |
| 2007/0065481 A1 | 3/2007 | Chudzik et al. | |
| 2007/0077271 A1 | 4/2007 | Dornish et al. | |

* cited by examiner

*Primary Examiner* — Nicholas Lucchesi
*Assistant Examiner* — Melissa A Snyder
(74) *Attorney, Agent, or Firm* — Michael F. Scalise

(57) ABSTRACT

An introducer assembly includes a sheath and a dilator. A biodegradable shroud covers the distal portion of the introducer assembly on the surface of both the sheath and the dilator. The biodegradable shroud dissolves in blood after being exposed for a predetermined time. Afterwards, the dilator can be separated from the sheath without breaking the sheath. The shroud improves movement of the introducer assembly through a venous system by preventing body tissue from getting caught in the space between the dilator and the shroud, for example should a "fish mouth" separation occur between them.

21 Claims, 7 Drawing Sheets

BIODEGRADABLE SHROUD FOR A DILATOR/SHEATH ASSEMBLY

CROSS-REFERENCE TO RELATED APPLICATION

This application claims priority from U.S. Provisional Application Ser. No. 61/022,651, filed Jan. 22, 2008.

TECHNICAL FIELD

The present invention relates to introducers and introducer assemblies, and more specifically to an introducer assembly including a dilator received in the lumen of an introducer sheath. A biodegradable shroud is provided on the distal portion of the introducer assembly where the dilator extends beyond and out from the sheath.

BACKGROUND OF THE INVENTION

Introducer devices provide for access to the vascular system. They are employed for inserting medical devices such as catheters, guidewires, leads, infusion ports, dialysis ports, dialysis catheters, and other such devices into the vascular system. A typical procedure for gaining access to the central venous system or the arterial system with an introducer is the Seldinger Introduction Method. The Seldinger Method provides for insertion of a hollow needle into the vasculature of a patient. A guidewire is inserted through the needle, and the needle is removed over the guidewire, leaving the guidewire in the vessel. The introducer assembly including the dilator and the introducer sheath is inserted over the guidewire into the vessel. The introducer assembly is advanced into a suitable position within the vessel, i.e. so that the introducer's distal end is well within the vessel but the proximal end of the introducer assembly is outside the patient. With the introducer assembly in the vessel, the guidewire and dilator are removed sequentially, leaving only the introducer sheath in the vessel. The introducer sheath is left in position and therefore offers direct access from outside the patient into the blood vessel lumen. The desired medical device is inserted through the lumen of the sheath into the appropriate vessel, and is implanted at the desired location within the body. To minimize any disturbance to the medical device, the sheath is removed from the medical device by cracking apart the handle, and peeling apart the sheath. Such removal techniques are well known by those skilled in the art.

During insertion of the introducer assembly including the dilator/introducer sheath into the body along the guidewire, the distal end of the introducer has to pass through various types of body tissue and anatomy. Sometimes the body tissues are rigid. This can cause significant resistance to movement of the introducer assembly through the vasculature. If resistance is great enough, the distal portion of the introducer sheath can be damaged, resulting in an introducer that may not be able to be inserted to its desired location in the body, or that could become damaged to a point that it is non-functional. The larger the diameter of the introducer sheath the greater the opportunity for the introducer to encounter resistance as it passes through body tissue.

To reduce the chance of such damage being caused by different anatomical tissues during insertion of an introducer assembly, the distal ends of the introduce sheath and the dilator received therein are designed with tapers that provide a transition from the larger diameter portion of the introducer sheath to a more distal portion of the dilator having a reduced diameter with the tapered profile. While the tapers generally allow the introducer to enter the body with reduced resistance, the tapered transition between the introducer sheath and the dilator in an introducer assembly is still a primary source of resistance. When the cross sectional area of the transition between the dilator and introducer sheath increases, for example, when only the tip of the dilator bends in a curved blood vessel during insertion while the introducer sheath maintains a relatively straight shape, the resistance from this transitional area can increase significantly.

What would be desirable is an introducer assembly comprising a dilator/introducer sheath designed to have minimum resistance at its tapered distal end during insertion into the body. What would also be desirable is easy removal of the dilator from the sheath after insertion of the introducer assembly into the body.

BRIEF DESCRIPTION OF THE DRAWINGS

FIG. 2A illustrates an expanded partial sectional view of the indicated area in FIG. 2.

DESCRIPTION OF THE PREFERRED EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
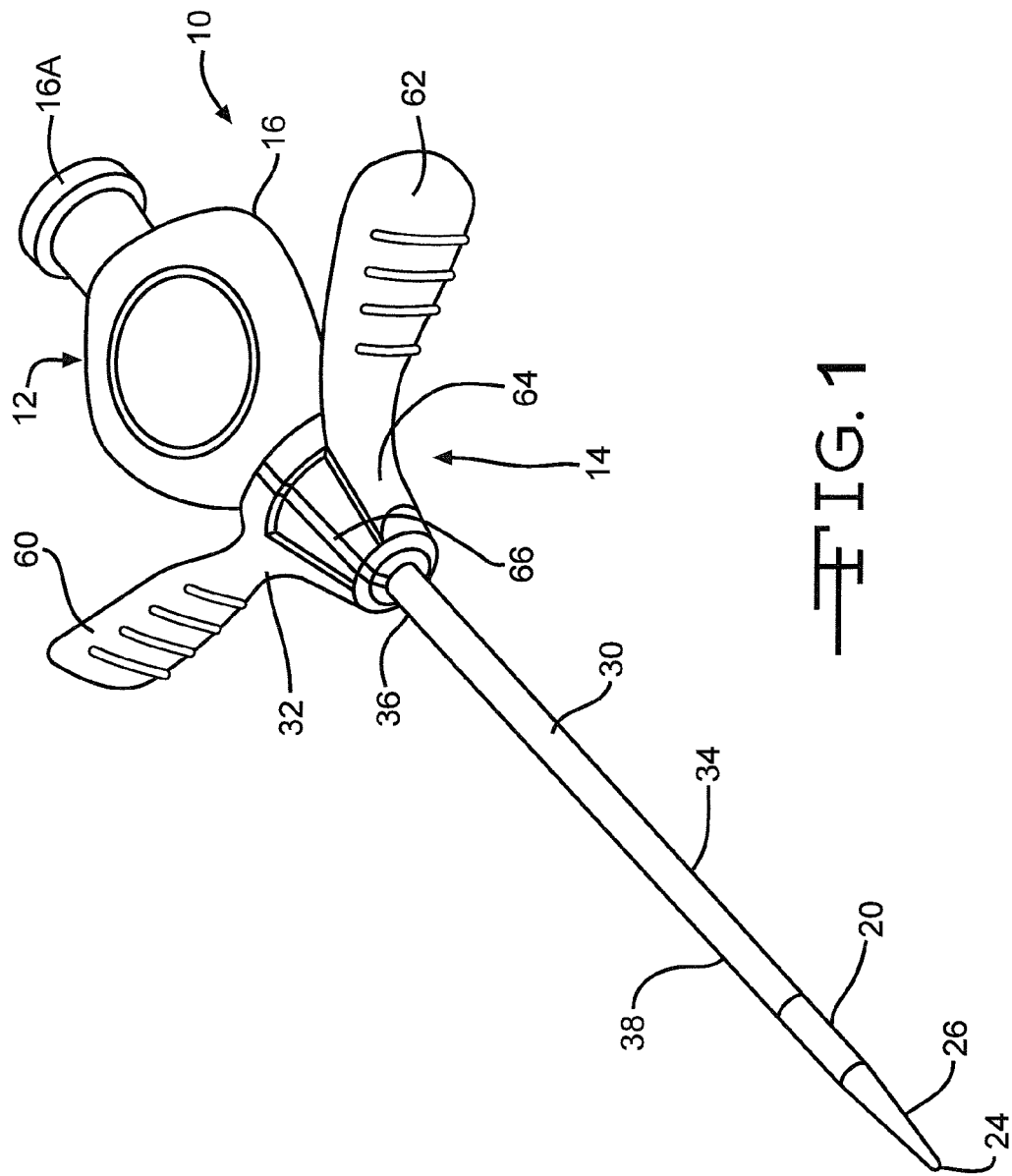
FIG. 1 illustrates a perspective view of a conventional introducer assembly 10 comprising a dilator 12 and an introducer sheath 30.

Turning now to the drawings, FIG. 1 illustrates an introducer assembly 10 comprising a dilator 12 disposed inside an introducer 14. The dilator 12 has a dilator handle 16 supported at the proximal end of a dilator tube 18 (FIGS. 4 to 7). The dilator tube 18 comprises a dilator sidewall 20 surrounding a lumen extending along the entire length thereof including the handle 16 to a distal portion 22 having an open end 24. The dilator tube 18 has a uniform circular cross-section normal to the longitudinal axis of the sidewall 20 extending along the majority of its length from the handle 16 to the distal portion 22. There, the dilator sidewall 20 has a taper 26 that progressively narrows to the distal open end 24 of a reduced diameter. However, the lumen through the dilator 12 including the handle 16 and the tube 18 is of a uniform diameter. This means that the thickness of the sidewall 20 becomes thinner at the distal portion 22 to provide the taper 26 to the distal open end 24. The dilator 12 is formed of, in an example, high density polyethylene, polypropylene, polyurethane, or fluorinated polymers such as, but not limited to, PTFE (polytetrafluoroethylene), FEP (fluorinated ethylene-propylene).

The introducer 14 comprises an introducer sheath 30 that is coupled with a handle 32. The introducer sheath 30 is comprised of a tubular sidewall 34 surrounding an open passage extending from a sheath proximal portion 36 supported by the handle 32 to a sheath distal portion 38. The sheath distal portion 38 has a taper 40 that progressively narrows from a larger outer diameter extending along a majority of the length of the sheath tubular sidewall 34 to an open sheath end 42 of the distal portion 38. As with the distal portion 22 of the dilator 12, the diameter of the sheath lumen does not reduce in diameter along its entire length. This means that the taper 40 is formed by a reduction in the thickness of the tubular sidewall 34 from one thickness along the majority of the length thereof to a reduced thickness at the open sheath end 42.

Figure 3:
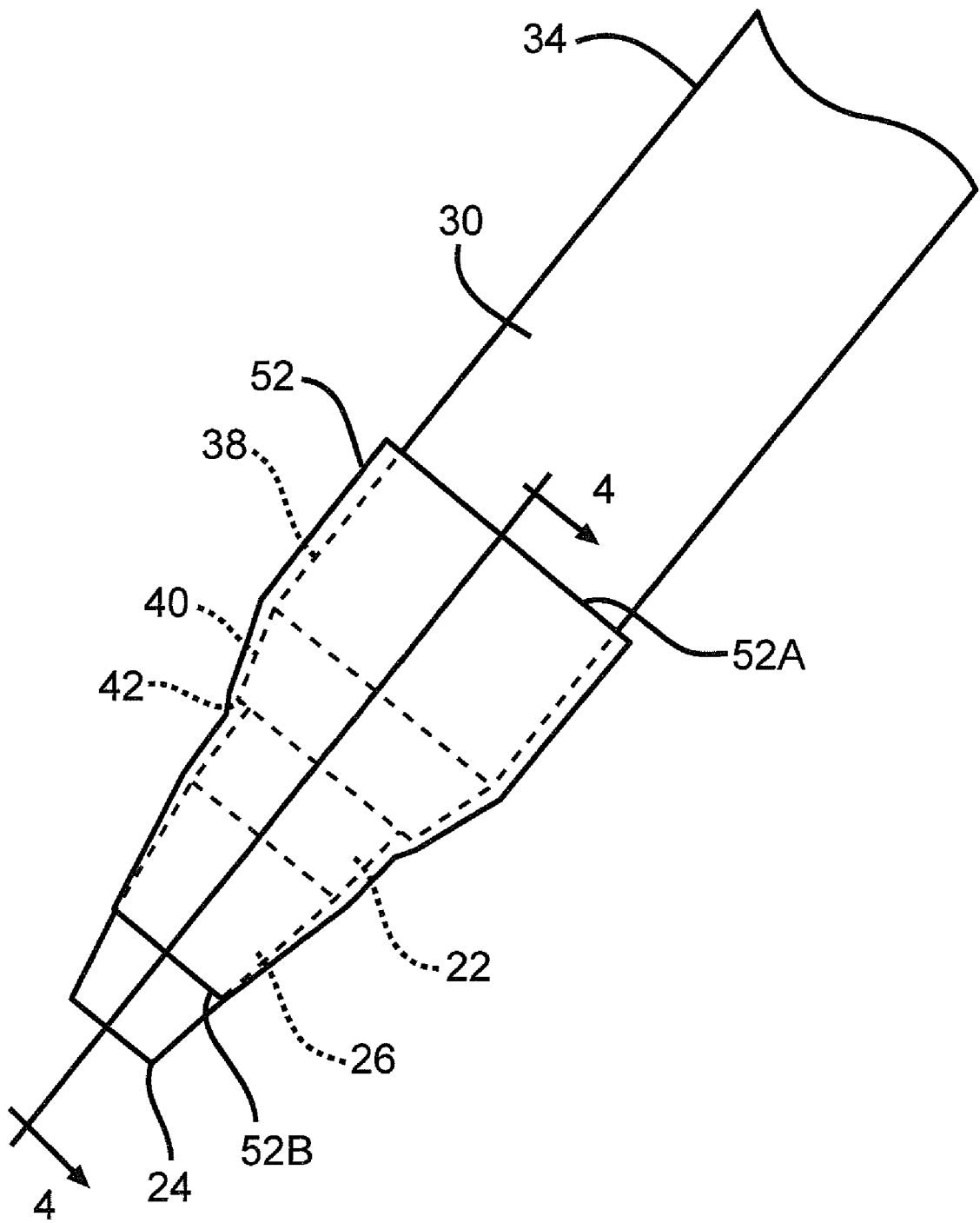
FIG. 3 illustrates a top view of the distal end of the introducer assembly 10 shown in FIG. 1 including a shroud 52 constructed in accordance with one embodiment of the current invention.
Figure 4:
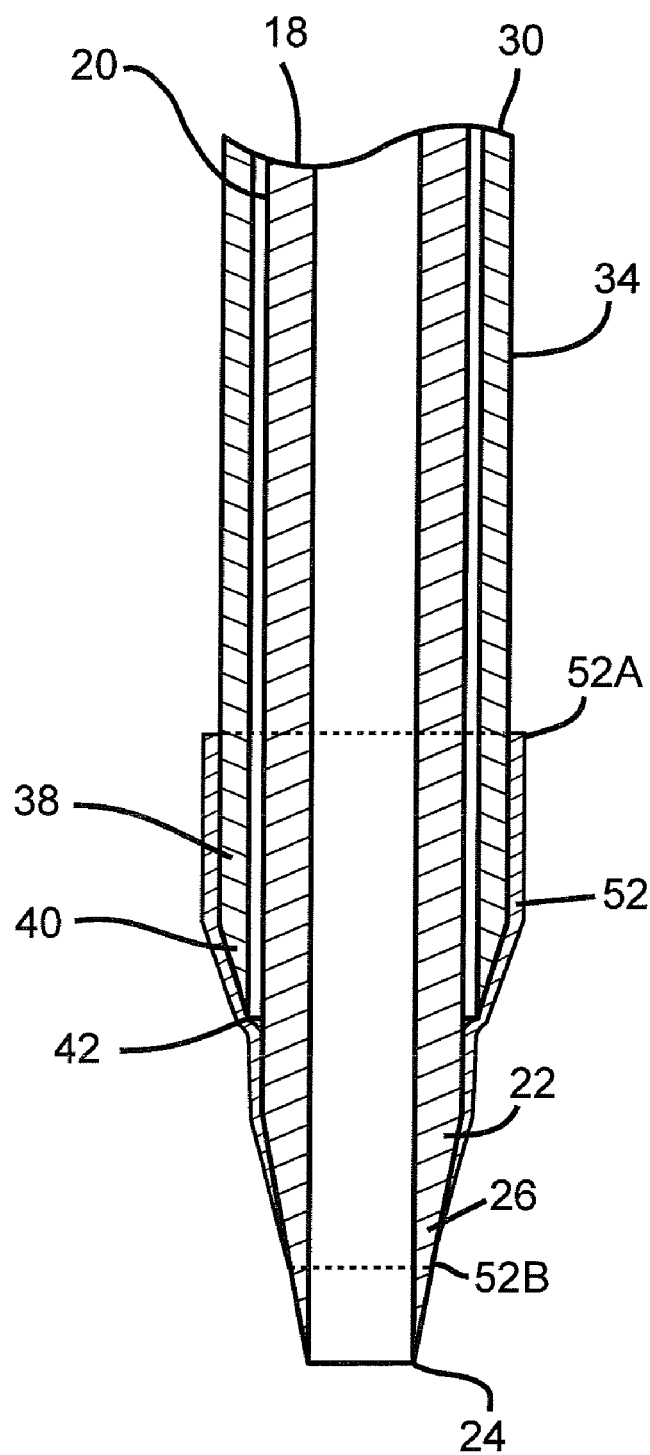
FIG. 4 is a partial cross-sectional view taken along line 4-4 of FIG. 3.

In that respect, the taper 40 (FIGS. 3 to 5) provides a slender profile from the introducer sheath 30 to the dilator 12 disposed through the sheath lumen. Similarly, the dilator taper 26 facilitates insertion of the introducer assembly 10 into a patient, for example, over a guidewire 44. The dilator handle 16 optionally includes features, such as a luer hub or threads 16A, that allows for other devices to be coupled thereto.

The introducer sheath 30 is formed of, in an example, fluorinated polymers such as, but not limited to, PTFE (polytetrafluoroethylene) and FEP (fluorinated ethylene-propylene), and non-fluorinated polymers, such as, but not limited to, polyethylene, polypropylene, nylon or polyimide. The sheath material, such as PTFE, can be molecularly oriented for optionally splitting the introducer sheath 30. Molecularly oriented sheaths do not necessarily require an additional mechanical scoring operation to produce split lines, as in the case of a polyethylene sheath. Instead, the oriented molecules allow the introducer sheath 30 to naturally peel like a banana. The introducer handle 32 is typically provided with diametrically opposed score lines or some similar form of linear weakening to facilitate its removal along with the introducer sheath 30.

Figure 2:
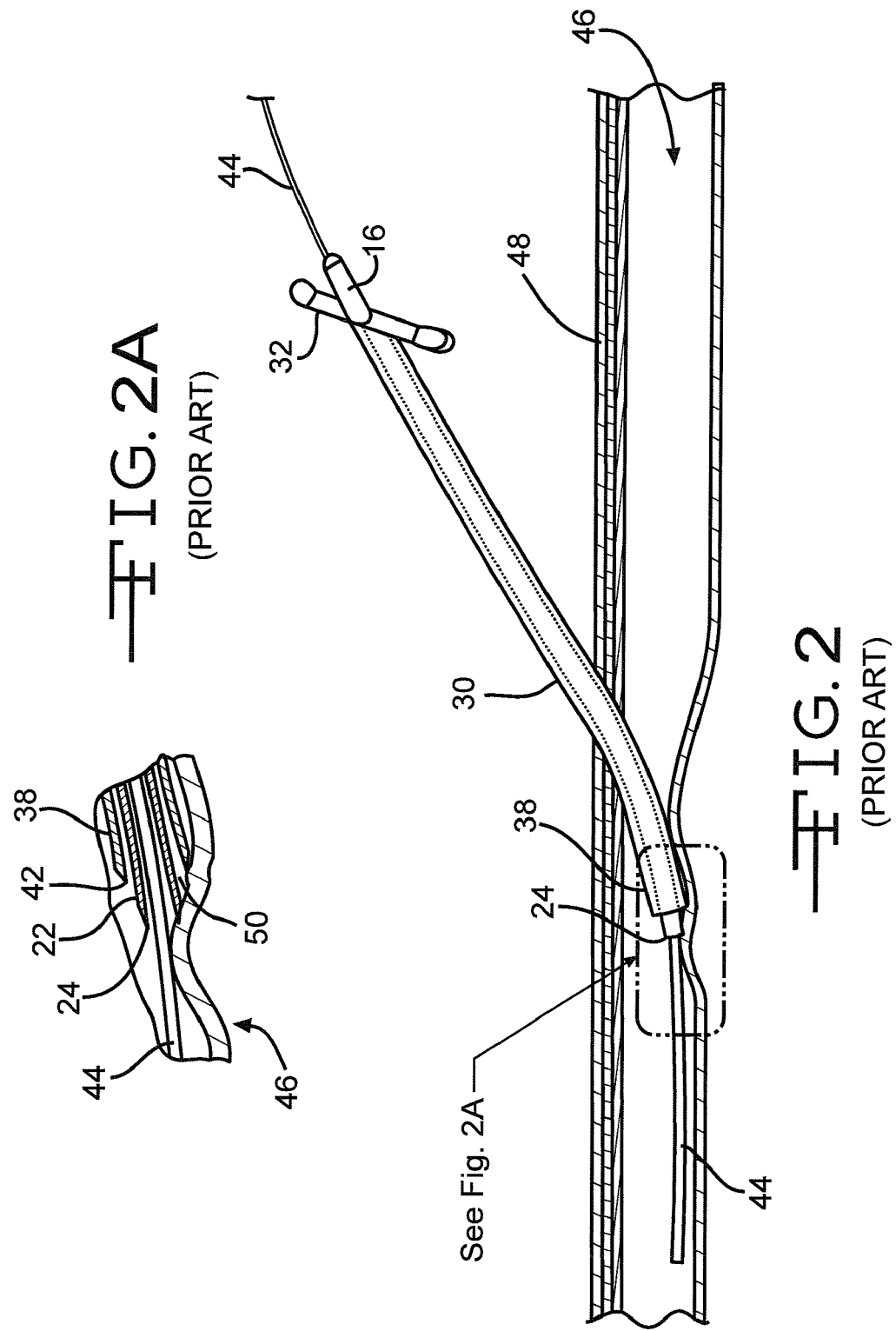
FIG. 2 illustrates a partial sectional view of the introducer assembly 10 shown in FIG. 1 being placed inside a blood vessel 46 along a guidewire 44.

FIGS. 2 and 2A depict the introducer assembly 10 shown in FIG. 1 including the dilator 12 received inside the lumen of the introducer sheath 14 being inserted into a body over a guidewire 44 according to the prior art. In this exemplary illustration, the body is part of the venous system 46. According to the previously described Seldinger Introduction Method, a hollow needle (not shown) is first inserted into the venous system 46 crossing the skin 48 and other tissue until its distal end is in a desired location. The guidewire 44 is next inserted into the venous system 46 through the needle, and the needle is removed over the guidewire, leaving the guidewire in the vessel. The introducer assembly 10 including the dilator 12 partially housed inside the introducer 14 is inserted over the guidewire 44 into the venous system 46 and advanced to a suitable position so that the distal portion 38 of the introducer sheath 30 is well within the vessel but both the dilator handle 16 and the introducer handle 32 are outside the patient. With the introducer assembly 10 in the vessel, the guidewire 44 and dilator 12 are removed sequentially, leaving only the introducer sheath 30 therein.

Even though the introducer assembly 10 encounters a variety of different tissue layers providing varied levels of resistance, the taper 40 at the distal portion 38 of the introducer sheath 30 narrowing down to the taper 26 at the distal portion 22 of the dilator 12 normally facilitates relatively easy insertion of the introducer assembly 10 into the body. The distal portion 22 of the dilator 12 and the distal portion 38 of the introducer sheath 30 normally bend upon entering the blood vessel 46 and as they follow the path of the guidewire 44. However, as shown in FIG. 2A, in some cases this distal bending may create a zone of increased "fish mouth" separation 50 between the dilator's distal portion 22 and the introducer sheath's distal portion 38 as the introducer assembly 10 encounters different tissue layers. This separation 50 can occur if the bending force exerted by the tissue, or the blood vessel wall, on the distal open end 24 of the dilator 12 is higher than that on the distal open end 42 of the sheath 30. Typically the mechanical strengths of the respective distal ends of the dilator 12 and the introducer sheath 30 are different. Different materials of construction for the dilator 12 and the introducer 14 can cause this, or there may be dimensional differences between their respective open ends.

As shown in FIG. 2A, this separation 50 can cause the distal open end 42 of the introducer sheath 30 to cut into tissue during advancement of the introducer assembly 10 along the insertion path of the guidewire 44, resulting in internal bleeding. Tissue can also get caught in the distal open end 42 of the introducer sheath 30 and impede advancement of the introducer assembly 10 along the guidewire 44. If the impeding force is high enough, the distal portion 38 of the introducer sheath 30 can be deformed or even damaged.

Referring now to FIGS. 3 to 7, the introducer assembly 10 previously illustrated in FIG. 1 is shown provided with a biodegradable shroud 52 according to the present invention. The shroud 52 continuously covers the distal portion 38 of the introducer sheath 30 and extends over at least some of the distal portion 22 of the dilator 12. The shroud 52 is preferably of a biodegradable material that is conformably deposited on the introducer assembly 10 to continuously cover the distal portion 38 of the introducer sheath 30 to a position proximate the open end 24 of the distal dilator portion 22. Preferably, the shroud 52 tapers from a shroud proximal end 52A to a shroud distal end 52B. This not only helps minimize resistance of the dilator 12 and introducer sheath 30 to movement through the vasculature 46, but also resistance attendant to the shroud 52 itself is minimized.

Examples of degradable materials include, but are not limited to, mannitol (hexan-1,2,3,4,5,6-hexol ($C_6H_8(OH)_6$) is a sugar alcohol or a polyol), gelatin, starch, cellulose, alginate, hyaluronic acid, polylactides (PLA), polyglycolides (PGA), polycaprolactone (PCL) and copolymers, non-cross linked water soluble salts of chitosan, or inorganic salt, such as sodium chloride mixtures, and combinations thereof. As used herein, the term "degradable" refers to a partial or a complete degradation of the material integrity of the shroud 52, which occurs through contact with blood or other body fluids. Such degradation can include dissolution, hydrolytic degradation, bioabsorption, and other degradation mechanisms well known to those skilled in the art.

Figure 6:
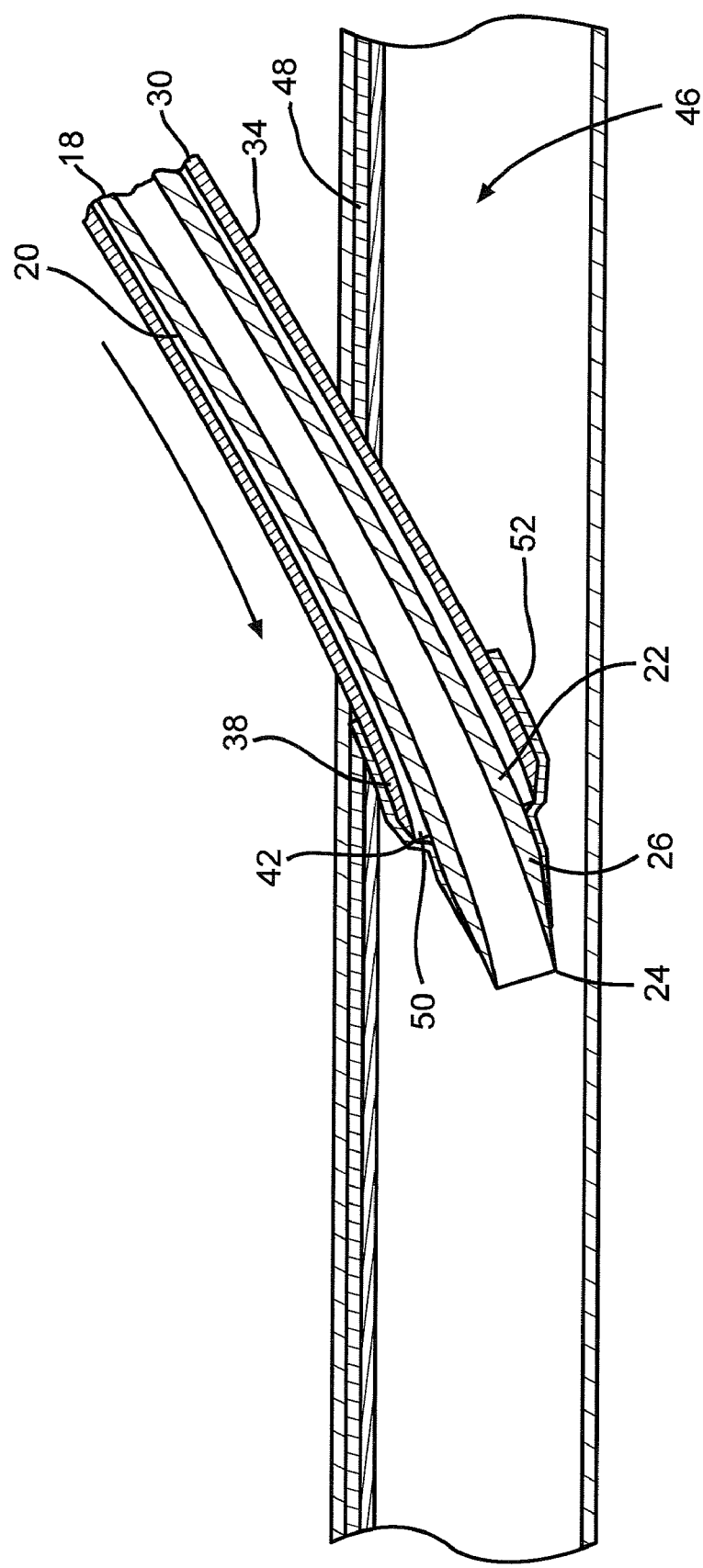
FIG. 6 illustrates a partial sectional view of the introducer assembly 10 provided with the shroud 52 shown in FIG. 3 after having been inserted into a blood vessel 46.

FIG. 6 illustrates insertion of the introducer assembly 10 including the shroud 52 into a blood vessel 46 after crossing the skin 48 and other tissue layers. The thin shroud 52 covers the distal portion 38 of the introducer sheath 30 including the open sheath end 42 and extends along a majority of the length of the distal portion 22 of the dilator 12. Underneath the shroud 52, if there is any separation 50 created between the distal open sheath end 42 and the distal portion 22 of the dilator 12 during bending of the introducer assembly 10 in the blood vessel 46, the shroud 52 prevents direct contact between the open sheath end 42 and the tissue. In that manner, the shroud 52 virtually eliminates any possibility that blood vessel tissue will be damages by the open sheath end 42 at the separation zone 50. In a preferred embodiment, the shroud 52 is made of a material having a thickness of from about 0.01 mm to about 1 mm and that degrades after contact with blood within a pre-determined period of time. Use of the shroud 52 is in direct contrast to the potentially damaging situation illustrated in FIGS. 2 and 2A.

The shroud 52 can be made by any one of a number of coating processes including, but are not limited to, dip coating, spray coating, and vapor deposition. The shroud 52 can also be attached to the distal portions 22 and 38 of the introducer assembly 10 as a prefabricated thin film. Attaching methods includes, but are not limited to, gluing, heat reflow and mechanical interference fitting.

The maximum pre-determined time for a partial or a complete degradation of the shroud 52 should be less than 30 seconds. The preferred time is about 15 seconds with the actual degradation period being controlled by the selection of the degradable material and the thickness of the shroud material, especially at the dilator/sheath transition. To achieve degradation within 30 seconds, a shroud 52 comprising mannitol should have a thickness of from about 0.03 mm to about 0.1 mm.

Figure 7:
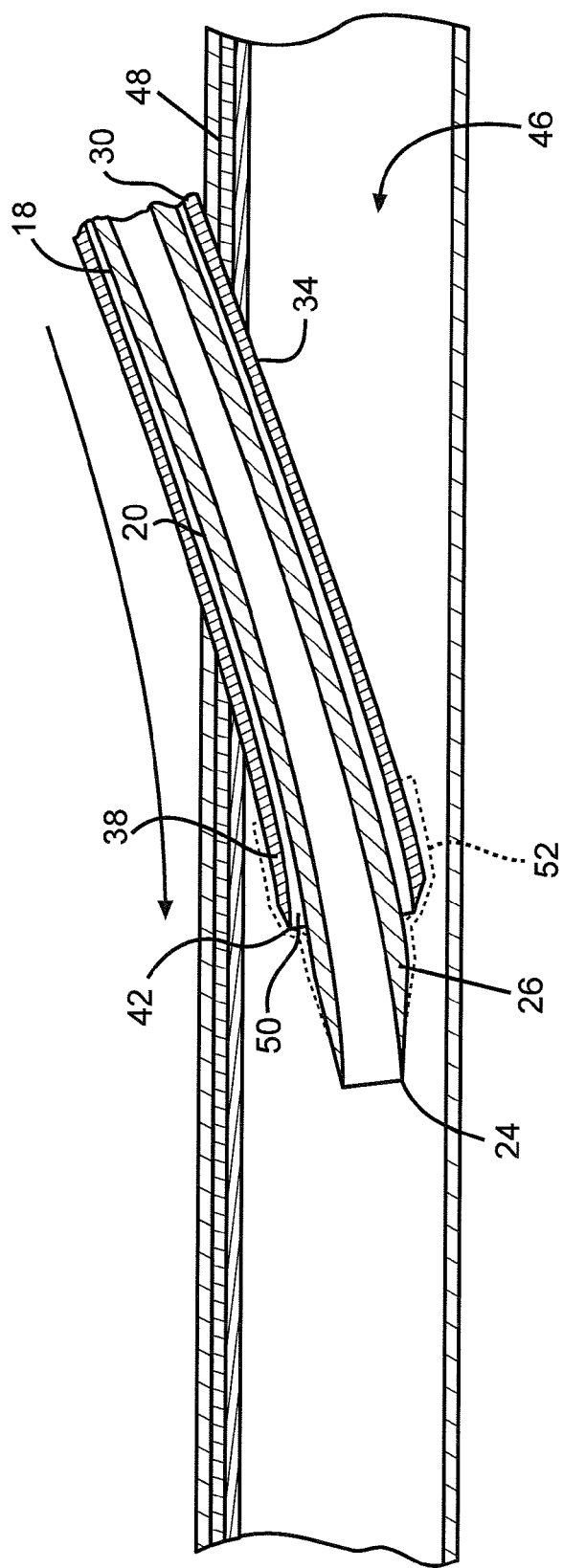
FIG. 7 illustrates a partial sectional view of the introducer assembly 10 provided with the shroud 52 shown in FIG. 6 as the shroud is being degraded inside the blood vessel 46.

FIG. 7 illustrates the biodegradable shroud 52 in a partially degraded condition after being placed inside the blood vessel 46. In the case of partial degradation, the shroud 52 is weakened through contact with blood to enable relatively easy separation and removal of the dilator 12 from the introducer sheath 30 after introducer placement. This weakening is associated with one or more of a combination of the degradation mechanisms discussed above.

Figure 5:
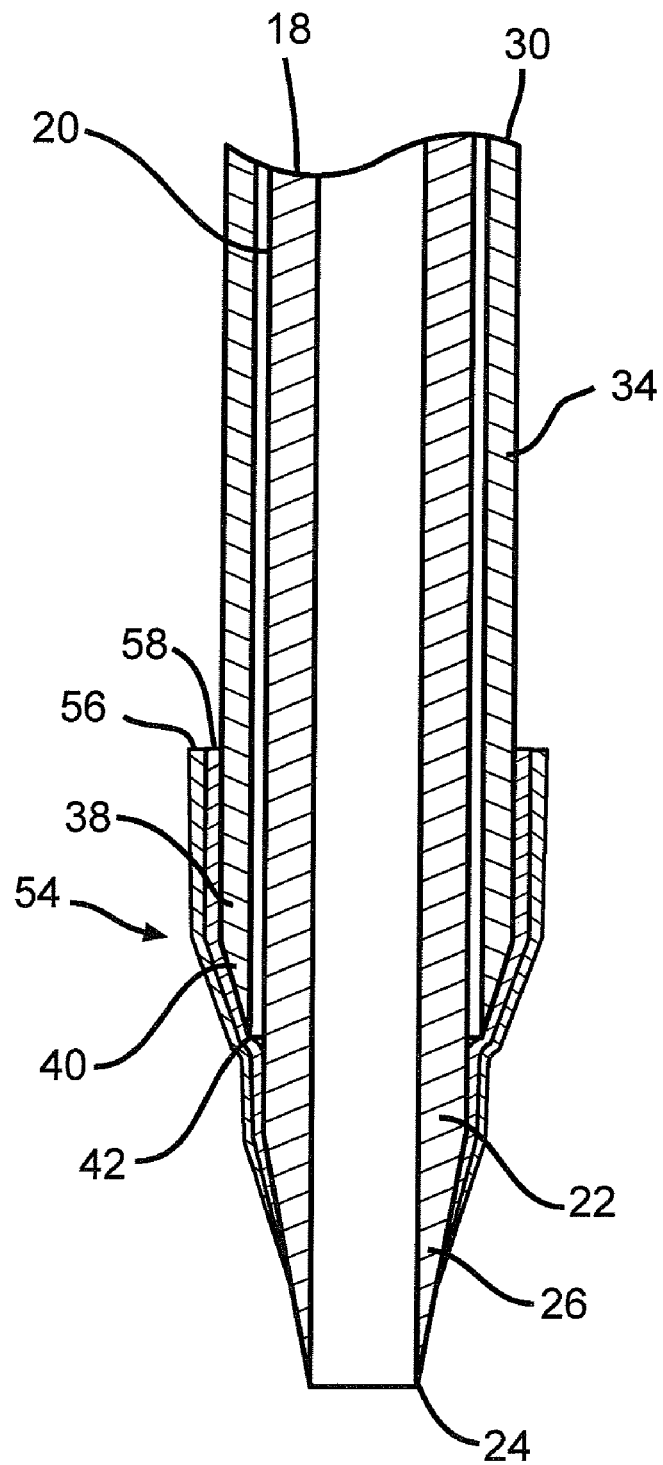
FIG. 5 is a partial cross-sectional view of the introducer assembly 10 shown in FIG. 1 provided with another embodiment of a shroud 54 constructed in accordance with the present invention.

FIG. 5 illustrates a further embodiment of a shroud 54 according to the current invention. The shroud 54 is composed of an outer layer 56 and an inner layer 58. Multi-layer structures can be used to fine tune the shroud's required mechanic strength during insertion, and the required speed of degradation after insertion. For an exemplary two layer structure, the distal portion 38 of the introducer sheath 30 housing the distal portion 22 of the dilator 12 is dip coated in a 15 wt % mannitol aqueous solution to form the inner layer 58 having a thickness of about 0.05 mm. This sub-assembly is then dip coated in a second mannitol aqueous solution containing 10 wt % of mannitol and 10 wt % of sodium chloride (NaCl). The second outer layer has a thickness of about 0.1 mm.

It should be understood that different degradable materials having different degradation periods and mechanical strengths can be selected to build the shroud 54 from the inner layer 58 to the outmost layer 56. While FIG. 5 illustrates a shroud 54 comprising two layers 56, 58, that should not be viewed as limiting. Shrouds of three or more layers are contemplated by the scope of the present invention. However, in any such multi-layer construction, it's preferred that the outer layer 56 degrades faster than the inner layer 58. Having a multi-layer shroud construction may be beneficial to tailor the slip resistance and structural integrity of the shroud. For example, it may be beneficial to provide the outer layer 56 with a high degree of lubricity, but that may detrimentally impact its structural integrity. A lack of structural integrity can be compensated for by having the inner layer 58 being somewhat more durable than the outer layer 56.

After the introducer assembly 10 is inserted in the vasculature system 46 to its intended location and the shroud 52 has degraded to a significant extent, the dilator 12 is removable from the introducer sheath 30 to allow other instruments to enter the blood vessel through the sheath inner lumen. The medical procedure is then performed in its normal manner, for example, placement of a cardiac lead, and the like.

Once the lead is in place and the introducer is no longer needed, the physician removes the introducer 14 without disturbing the lead. This is done by holding the wings 60, 62 of the introducer 14 shown in FIG. 1 between the thumb and fore finger and counter rotating them with respect to each other while slowly moving the wings further apart. The introducer valve housing 64 including a valve membrane (not shown) supported therein is readily separated. This occurs at a score line 66 running along the valve housing 64 and the valve membrane supported therein.

In a preferred embodiment of the introducer assembly 10, the tubular sidewall 34 of the introducer sheath 30 does not require a score line. Instead, it is made of PTFE which has a unique molecular structure. Once a sufficient amount of force is exerted at opposed stress points (not shown) provided at the proximal end of the tubular sidewall 34 underneath the valve housing 64, the PTFE molecules begin to sever. Further pulling force causes the resulting tear to propagate in a linear manner along the entire length of the sheath tubular sidewall 34 to its distal end 42. The tear is extremely straight and parallel to the longitudinal axis of the sheath 14. Importantly, the tear is smooth and provides the physician with an even tactile feel that gives the physician a high degree of confidence that the lead, and the like, was not disturbed during removal of the introducer 14 from the venous system. 46. For a more detailed description of structures that are suitable for removing an introducer from a venous system, and the like, without disrupting a medical device inserted into the vasculature through the introducer, reference is made to U.S. Provisional Application Ser. No. 61/107,447, filed Oct. 22, 2008. This application is assigned to the assignee of the present invention and incorporated herein by reference.

Another technique for removing the introducer 14 is to pull it out of the venous system against the cutting edge of the slitter (not shown) as the lead or like medical device remains positioned in the body. This technique is well known by those skilled in the art.

It is to be understood that the above description is intended to be illustrative, and not restrictive. Many other embodiments will be apparent to those of skill in the art upon reading and understanding the above description. It should be noted that embodiments or portions thereof discussed in different portions of the description or referred to in different drawings can be combined to form additional embodiments of the present invention. The scope of the invention should, therefore, be determined with reference to the appended claims, along with the full scope of equivalents to which such claims are entitle.

What is claimed is:

1. An introducer assembly comprising:
    a) an elongate introducer sheath extending from a proximal portion to a distal portion, the elongate introducer sheath including a passage therethrough;
    b) an elongate dilator disposed through the introducer sheath passage and having a proximal portion and a distal portion, the dilator distal portion extending out of the sheath passage, tapered to a distal dilator end; and
    c) a biocompatible and biodegradable shroud covering the distal portions of the introducer sheath and of the dilator, wherein the shroud comprises:

i) a 15 wt % mannitol aqueous solution as an inner layer contacting the distal portions of the introducer sheath and of the dilator, and ii) an aqueous solution containing 10 wt % of mannitol and 10 wt % of sodium chloride (NaCl) as an outer shroud layer contacting the inner shroud layer.

2. The introducer assembly of claim 1 wherein the biodegradable shroud is soluble in body fluids.

3. The introducer assembly of claim 2 wherein the body fluid is blood in a blood vessel.

4. The introducer assembly of claim 1 wherein the shroud is substantially completely dissolved after being in body fluids for about 30 seconds.

5. The introducer assembly of claim 1 wherein the shroud is substantially completely dissolved after being in body fluids for about 15 seconds.

6. The introducer assembly of claim 1 wherein the shroud has a thickness ranging from about 0.01 mm to about 1 mm.

7. The introducer assembly of claim 1 wherein the shroud has a thickness that gradually increases from the dilator distal end to the sheath distal portion, forming a tapered outer shroud surface covering the dilator and the sheath distal portions.

8. An introducer assembly comprising:
a) an elongate introducer sheath extending from a proximal portion to a distal portion, the elongate introducer sheath including a passage therethrough;
b) an elongate dilator disposed through the introducer sheath passage and having a proximal portion and a distal portion, the dilator distal portion extending out of the sheath passage, tapered to a distal dilator end; and
c) a biocompatible and biodegradable shroud covering the distal portions of the introducer sheath and of the dilator, wherein the shroud comprises:
  i) an inner layer contacting the distal portions of the introducer sheath and of the dilator,
  ii) an outer shroud layer contacting the inner shroud layer, and
  iii) wherein the outer shroud layer is relatively more lubricous than the inner shroud layer and wherein the outer shroud layer is relatively more durable than the inner shroud layer.

9. The introducer assembly of claim 1 wherein the shroud has a thickness of from about 0.03 mm to about 0.1 mm.

10. The introducer assembly of claim 1 wherein the shroud inner layer has a thickness of about 0.05 mm and the shroud outer layer has a thickness of about 0.1 mm.

11. An introducer assembly comprising:
a) an elongate introducer sheath extending from a proximal portion to a distal portion, the elongate introducer sheath including a passage therethrough;
b) an elongate dilator disposed through the introducer sheath passage and having a proximal portion and a distal portion, the dilator distal portion extending out of the sheath passage, tapered to a distal dilator end; and
c) a biocompatible and biodegradable shroud having a thickness of from about 0.01 mm to about 0.1 mm covering the distal portions of the introducer sheath and of the dilator, wherein the shroud comprises:
  i) a 15 wt % mannitol aqueous solution as an inner layer contacting the distal portions of the introducer sheath and of the dilator, and
  ii) an aqueous solution containing 10 wt % of mannitol and 10 wt % of sodium chloride (NaCl) as an outer layer contacting the inner layer.

12. The introducer assembly of claim 11 wherein the shroud is substantially completely dissolved after being in body fluids from about 15 seconds to about 30 seconds.

13. The introducer assembly of claim 11 wherein the shroud has a thickness that gradually increases from the dilator distal end to the sheath distal portion, forming a tapered outer shroud surface covering the dilator and the sheath distal portions.

14. The introducer assembly of claim 11 wherein the shroud inner layer has a thickness of about 0.05 mm and the shroud outer layer has a thickness of about 0.1 mm.

15. A method for providing an introducer assembly, comprising the steps of:
a) providing an elongate introducer sheath extending from a proximal portion to a distal portion, the elongate introducer sheath including a passage therethrough;
b) positioning an elongate dilator through the introducer sheath passage, the dilator having a dilator proximal portion and a dilator distal portion extending out of the sheath passage and tapered to a distal dilator end; and
c) contacting the distal portions of the introducer sheath and the dilator with a biocompatible and biodegradable shroud, wherein the shroud comprises:
  i) a 15 wt % mannitol aqueous solution as an inner layer contacting the distal portions of the introducer sheath and of the dilator, and
  ii) an aqueous solution containing 10 wt % of mannitol and 10 wt % of sodium chloride (NaCl) as an outer layer contacting the inner layer.

16. The method of claim 15 including contacting the distal portions of the introducer sheath and the dilator with the biocompatible and biodegradable shroud by a technique selected from the group consisting of dip coating, spray coating, and vapor deposition.

17. The method of claim 15 including providing the biocompatible and biodegradable shroud as a prefabricated thin film contacted to the distal portions of the introducer sheath and the dilator by a technique selected from the group consisting of gluing, heat reflow, and mechanical interference fitting.

18. The method of claim 15 including providing the shroud inner layer having a thickness of about 0.05 mm and the shroud outer layer having a thickness of about 0.1 mm.

19. The method of claim 15 including providing the shroud having a thickness of from about 0.01 mm to about 0.1 mm.

20. The introducer assembly of claim 8 wherein the shroud is of a material selected from the group consisting of mannitol, gelatin, starch, cellulose, alginate, hyaluronic acid, polylactides (PLA), polyglycolides (PGA), polycaprolactone (PCL) and copolymers, non-cross linked water soluble salts of chitosan, sodium chloride mixtures, and combinations thereof.

21. The introducer assembly of claim 20 wherein the shroud is substantially completely dissolved after being in body fluids for about 30 seconds.

* * * * *